United States Patent [19]
Kluger et al.

[11] Patent Number: 5,399,671
[45] Date of Patent: Mar. 21, 1995

[54] SPECIFICALLY CROSSLINKED HEMOGLOBIN WITH FREE FUNCTIONALITY

[76] Inventors: Ronald Kluger, 14 Bradgate Road, Don Mills, Ontario, Canada, M3B 1J77; Yonghong Song, 30 Charles Street West, Toronto, Ontario, Canada, M4Y 1R5

[21] Appl. No.: 978,418

[22] Filed: Nov. 18, 1992

[51] Int. Cl.$^6$ .................. C07C 103/52; C07K 13/00; A61K 35/14
[52] U.S. Cl. ................................. 530/385; 530/402; 530/410
[58] Field of Search .................. 530/385, 402, 410; 514/6

[56] References Cited

U.S. PATENT DOCUMENTS

| | | | |
|---|---|---|---|
| 4,529,719 | 7/1985 | Tye | 514/6 |
| 4,584,130 | 4/1986 | Bucci et al. | 260/112 |
| 4,598,064 | 7/1986 | Walder | 514/6 |
| 4,857,636 | 8/1989 | Hsia | 530/385 |

FOREIGN PATENT DOCUMENTS

WO/92/217-02  5/1992  WIPO.

Primary Examiner—Lyle A. Alexander
Assistant Examiner—Rachel Freed

[57] ABSTRACT

Hemoglobin is site-specifically crosslinked into its tetrameric form by reaction with a trifunctional reagent which combines electrostatic effects, steric effects and the presence of functional groups so that two of the functional groups react with specific sites on the hemoglobin whilst the third site is left free for reaction with endogenous nucleophilic compounds. A specific example of such a crosslinking reagent is trimesoyl tris(3,5-dibromosalicylate), TTDS, which effects specific crosslinking between the amino groups of lysine-82 on each respective β sub-unit. While the crosslinking reagent TTDS has three available carboxyl groups for the crosslinking reaction, only two so react, leaving one free carboxyl for reaction with exogenous nucleophiles, e.g. to render the hemoglobin product useful as a carrier for nucleophilic compounds through the body's circulatory system.

9 Claims, 5 Drawing Sheets

SPECIFICALLY CROSSLINKED HEMOGLOBIN WITH FREE FUNCTIONALITY

FIELD OF THE INVENTION

This invention relates to modified hemoglobin, and processes and reagents for effecting modification of hemoglobin. More specifically, it relates to crosslinking of hemoglobin utilizing specific primary amino groups on sub-units of the hemoglobin to effect the crosslinking reaction, and to such crosslinked hemoglobin which is capable of chemical reaction with other reactive compounds in a specific and predetermined manner.

BACKGROUND OF THE INVENTION

Hemoglobin is a naturally occurring protein. When contained in red blood cells, hemoglobin exists in the form of a tetramer of four sub-units, two $\alpha$ sub-units and two $\beta$ sub-units. Each sub-unit has a protein chain and a heme molecule, the protein chains of the $\alpha$ sub-units containing 141 amino acids of known sequence and the protein chains of the $\beta$ sub-units containing 146 amino acids of known sequence. As a natural, bio-acceptable and well studied protein, hemoglobin is an attractive candidate for transport of bio active materials, drugs and other species in vivo, by attachment of such species to hemoglobin and introduction thereof into the circulatory system. Hemoglobin in solution outside the natural red blood cell, however, tends to dissociate from the tetrameric form into dimers and even monomers of the sub-units. These have too low a molecular weight to be adequately retained in circulation in the body. Accordingly, formation of chemical crosslinks between the sub-units of hemoglobin, to stabilize it in its natural tetrameric form, and hence ensure its adequate retention in the circulatory system, is necessary before hemoglobin can be developed as such a transport system.

In order to render a hemoglobin product properly acceptable in biomedical applications, control over its precise chemical nature is needed. Accordingly, it is desirable that any crosslinking which is effected between sub-units of hemoglobin is by means of specific and reproducible chemical linkages between specific sites or chemical groups on the hemoglobin molecules. With protein chains the size of those of the sub-units of hemoglobin, each containing substantial numbers of reactive primary amino groups, for example, this is difficult to achieve.

BRIEF REFERENCE TO THE PRIOR ART

U.S. Pat. No. 4,857,636 Hsia, describes a process in which hemoglobin is crosslinked by reaction with a polyaldehyde derived from ring opening oxidation of a saccharide. The resulting product is non-specific as regards its selection of crosslinking sites on the hemoglobin protein chains.

U.S. patent application Ser. No. 07/746,372 and its equivalent PCT application no. PCT/CA92/00221 Kluger et al., describe hemoglobin which is specifically crosslinked between the epsilon amino group of lysine-82 of a first $\beta$ chain of hemoglobin and the $\alpha$ amino group valine-1 of a second $\beta$ chain of the hemoglobin. Crosslinking reagents are used which have either two or three functional groups capable of reacting with primary amino groups on the hemoglobin chains. When a trifunctional reagent is used, a third crosslink is formed, specifically using the epsilon amino group lysine-82 of the second $\beta$ chain or the $\alpha$ amino group valine-1 of the first $\beta$ chain.

SUMMARY OF THE INVENTION

It is an object of the present invention to provide novel hemoglobins which are crosslinked between two specific sites on the sub-units, and are produced in an efficient manner.

It is a further object of the invention to provide processes and reagents for preparing such novel crosslinked hemoglobins.

According to one aspect of the present invention, a chemical reagent containing three or more reactive sites is reacted at two specific sites on hemoglobin, with the third reactive site of the reagent remaining available for further reaction with another compound altogether. This third reactive site does not react with an active site on any of the hemoglobin chains, despite the fact that it is chemically similar to the other two groups of the reagent. Reagents which accomplish this have a core hydrocarbon or substituted hydrocarbon group, with at least three bulky electrophilic anionic groups, to constitute leaving groups which react with primary amino groups on the hemoglobin chains. In practice, however, only two of the leaving groups react, leaving the third available for reaction with another compound. Useful such reagents correspond to the general formula where R represents an aliphatic, aromatic or alicyclic hydrocarbon radical; and X, Y and Z are the same or different and each represents a bulky, aromatic electrophilic anionic leaving group.

While it is not intended that this invention should be limited or bound to any specific theory or mechanism of operation, it is believed that the reagents described herein possess a combination of electrostatic properties, steric bulk and functional groups which provides a high degree of selectivity and efficiency in the crosslinking of hemoglobin.

Reagents according to the present invention react with human deoxyhemoglobin to crosslink the $\beta$ sub-units at position lys-82 of each sub-unit. The third reactive group on the reagent is available to react with exogenous nucleophiles.

BRIEF REFERENCE TO THE DRAWINGS

DESCRIPTION OF THE PREFERRED EMBODIMENTS

The crosslinking reagents used in the present invention thus comprise a core group R which is a hydrocarbon, preferably an aromatic hydrocarbon, and at least three bulky electrophilic anionic leaving groups. These leaving groups are preferably acyl-(substituted aromatic) groups in which the substituents are electron withdrawing groups such as halogen and carboxylate, to enhance the electrophilicity of the acyl group through which the leaving groups are linked to the core group R. Thus the preferred crosslinking reagents correspond to the general formula:

in which X', Y' and Z', which are the same or different, each represent an electrophilic anionic leaving group consisting essentially of an aromatic group carrying at least two electron-withdrawing groups. Examples of suitable electron-withdrawing groups include halogens, especially bromine, and carboxylate.

The specific, most preferred crosslinking reagent according to the present invention, is trimesoyl tris (3,5-dibromosalicylate), hereinafter TTDS.

Thus, according to a specific aspect of the present invention, there is provided hemoglobin crosslinked between lys-82 of each β chain, with a crosslinking reagent consisting essentially of trimesoyl tris(3,5-dibromosalicylate), of the chemical formula:

For convenience, the invention will be further described with specific reference to this crosslinking reagent.

When trimesoyl tris(3,5-dibromosalicylate) is reacted with hemoglobin according to the present invention, the crosslinked hemoglobin product can be represented thus:

where Lys-82' and 82-Lys represent the β chains of the crosslinked hemoglobin. There is retained on the TTDS residue a free carboxyl group available for reaction with exogenous nucleophiles, but which does not react, at least to any significant extent, with groups on the hemoglobin.

It is believed that the selectivity and efficiency of the crosslinking of hemoglobin by TTDS is a function of electrostatic effects, steric effects and the presence of additional functional groups.

Amino groups are good targets for directing crosslinking reagents but in the case of hemoglobin, each αβ dimer has 24 primary amino groups which can react, giving diverse products unless the reagent has further specificity. Anionic acylating reagents are known to show selectivity for certain amino groups within hemoglobin, particularly those located in the site which binds the polyanionic regulator, 2,3-diphosphoglycerate. The charge of such a reagent directs it to cationic sites on the protein, consistent with the known importance of electrostatic control of association in protein binding sites.

In addition to electrostatic effects, selectivity and efficiency can be enhanced by taking advantage of steric effects and the presence of additional functional groups. Steric effects play an important role in determining regioselectivity of organic reagents and such effects can increase the selectivity of a protein reagent. The combination of charge-direction, steric bulk, and multifunctionality in a single reagent TTDS leads to improved selectivity and yield, if the desired product results from reaction at the most accessible site.

Trimesoyl tris(3,5-dibromosalicylate), TTDS, is a reagent which combines all the features discussed above: it is anionic, bulky and trifunctional. TTDS reacts with both deoxy and carbonmonoxy human hemoglobin to give products which indicate that the reaction is effectively controlled by both charge and steric bulk of the reagent. The additional functional group provides statistical advantages in the initial reaction and entropic advantages in forming the crosslink.

The reaction of TTDS with hemoglobin is highly selective for the epsilon-amino groups of the Lys-82 residues of each of the β sub-units. Integration of the chromatograms of the reaction products indicates a yield of about 85% of the products resulting from crosslinking of these residues. These are in the site which normally binds the polyanionic effector, 2,3-diphosphoglycerate (DPG). The residue is very accessible to bulky reagents since its epsilon-amino group is at the end of a primary alkyl chain in a large cavity of the protein tetramer. In deoxyhemoglobin, the DPG binding site is expanded relative to the carbonmonoxy and oxy forms, separating the $\beta$ chains and moving the Lys-82 residues. If the third dibromosalicylate ester group is less mobile in the deoxy crosslinked species it is also less accessible for hydrolysis than in the carbonmonoxy form where the residues are more flexible. Another possibility is that in the carbonmonoxy hemoglobin, the third carboxyl could be held outside the DPG site by steric limitations.

The bifunctional crosslinker, fumaryl bis(3,5-dibromosalicylate), FBDS, reacts with oxyhemoglobin to give as a primary product ($\beta$82Lys-fumaryl-Lys82$\beta'$) hemoglobin in which the crosslink is between epsilon-amino groups. The reaction of deoxyhemoglobin with FBDS gives a mixture of major products. Thus, the trifunctional nature of TTDS adds specificity beyond that of a related bifunctional material with the same leaving group.

Figure 1:
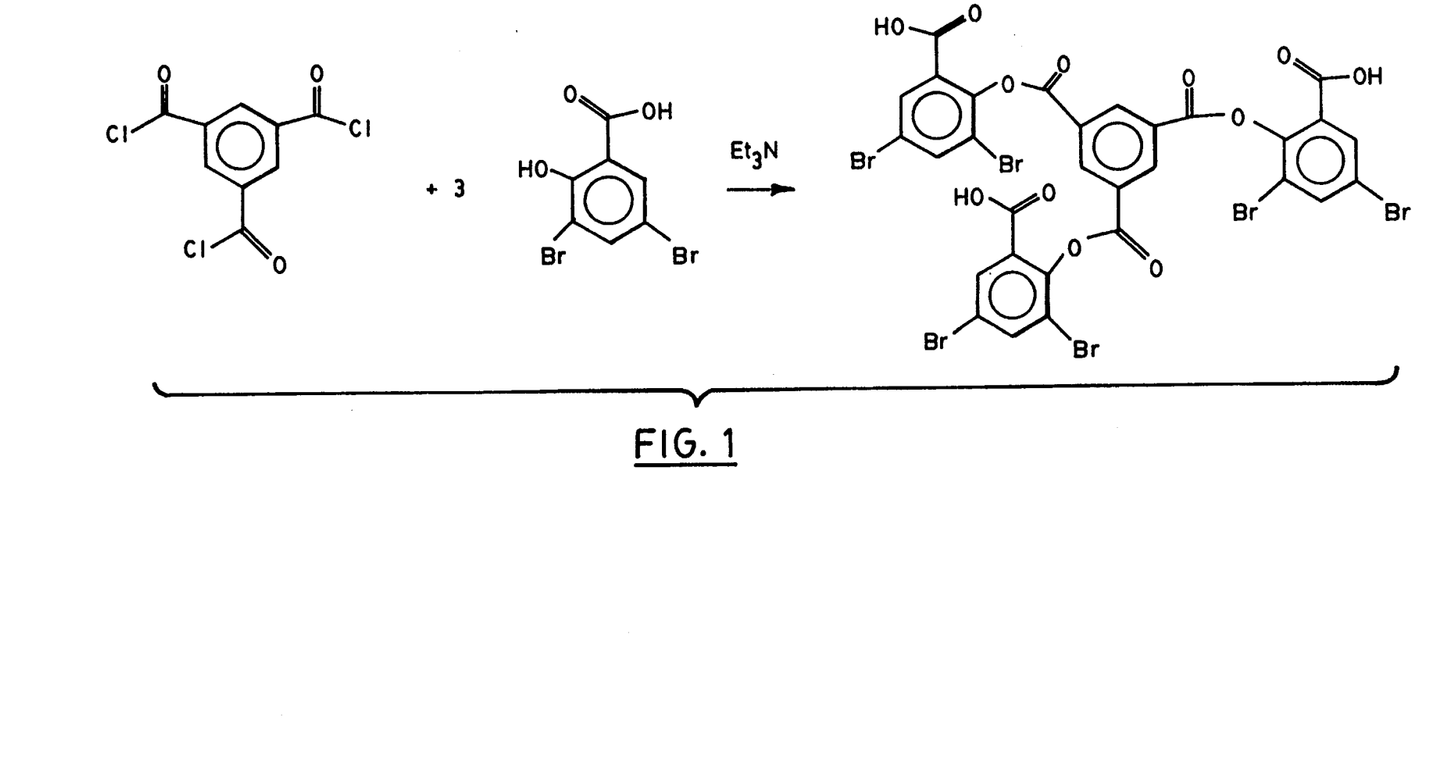
FIG. 1 is a reaction scheme showing a direct synthesis route for the exemplary reagent trimesoyl tris (3,5-dibromosalicylate), TTDS.
Figure 2:
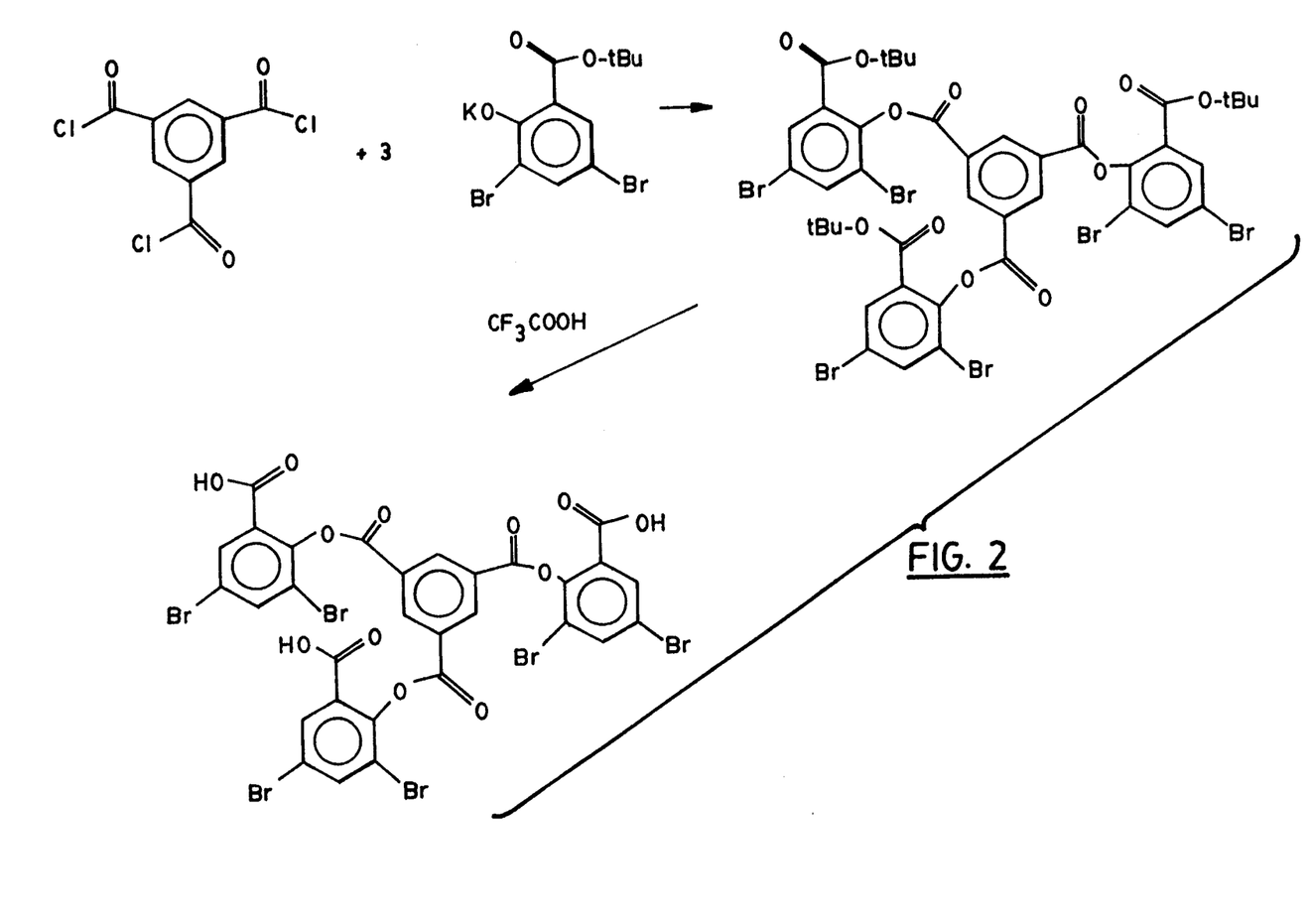
FIG. 2 is a preferred reaction scheme for preparing TTDS.
Figure 3:
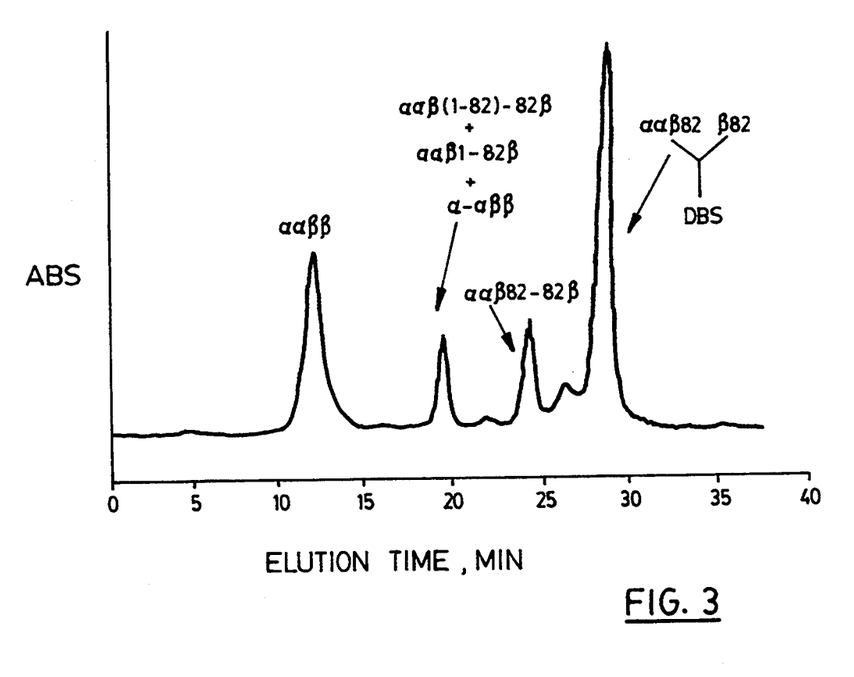
FIG. 3 is an AX-300 ion exchange HPLC chromatogram of reaction products from TTDS and deoxyhemoglobin, reacted at 35° C. for two hours, Example 3 below. Native hemoglobin is "$\alpha\alpha\beta\beta$". The peaks are indicated by the modification of hemoglobin. "$\alpha\alpha\beta 82$-$82\beta$" is crosslinked by the trimeric functionality and has the third salicylate hydrolyzed to the free acid. "DBS" indicates that the salicylate ester is still intact at the third carboxyl group (while the other two groups have formed amides with hemoglobin). Peak identification is by globin chain separation and peptide analysis.
Figure 4:
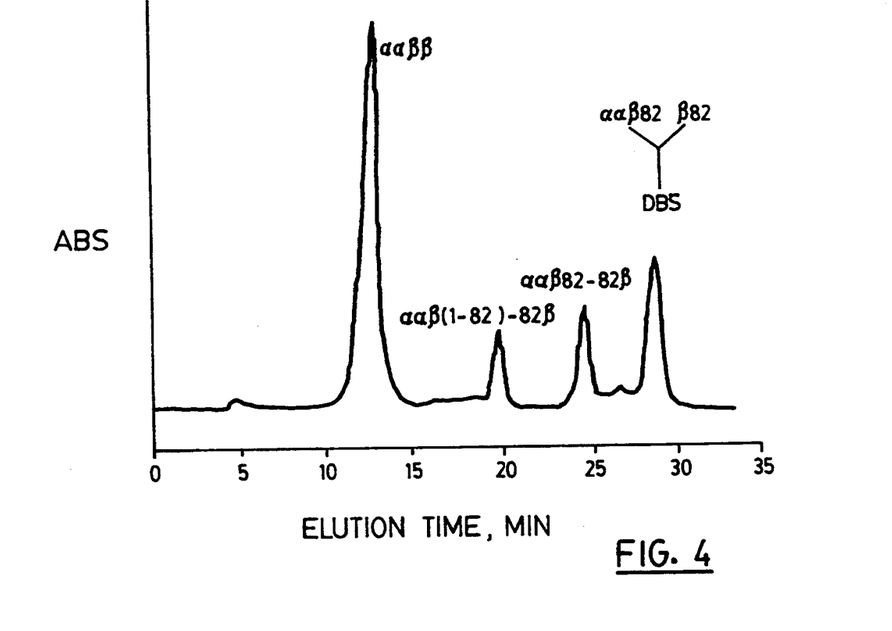
FIG. 4 is an AX-300 profile for reaction of TTDS with carbonmonoxyhemoglobin at 35° C., after two hours, Example 3 below.
Figure 5:
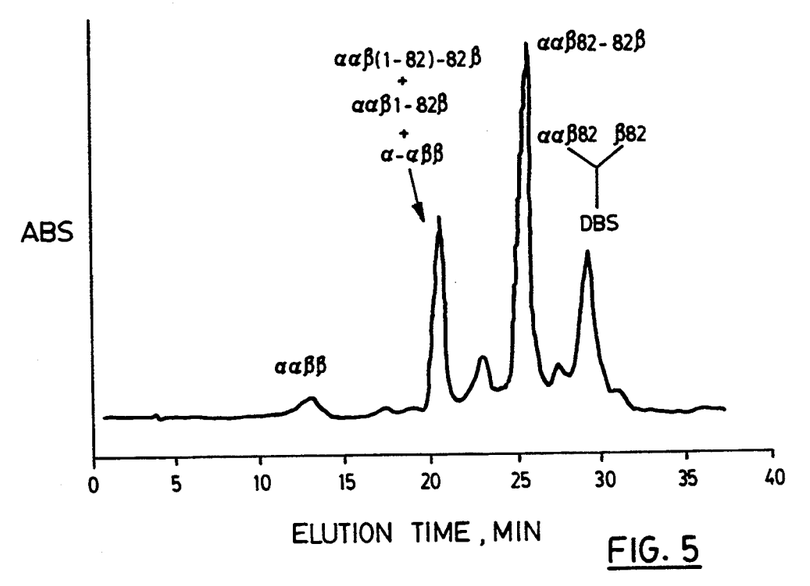
FIG. 5 is an AX-300 profile for reaction of TTDS with deoxyhemoglobin at 60° C. for two hours, Example 3 below.
Figure 6:
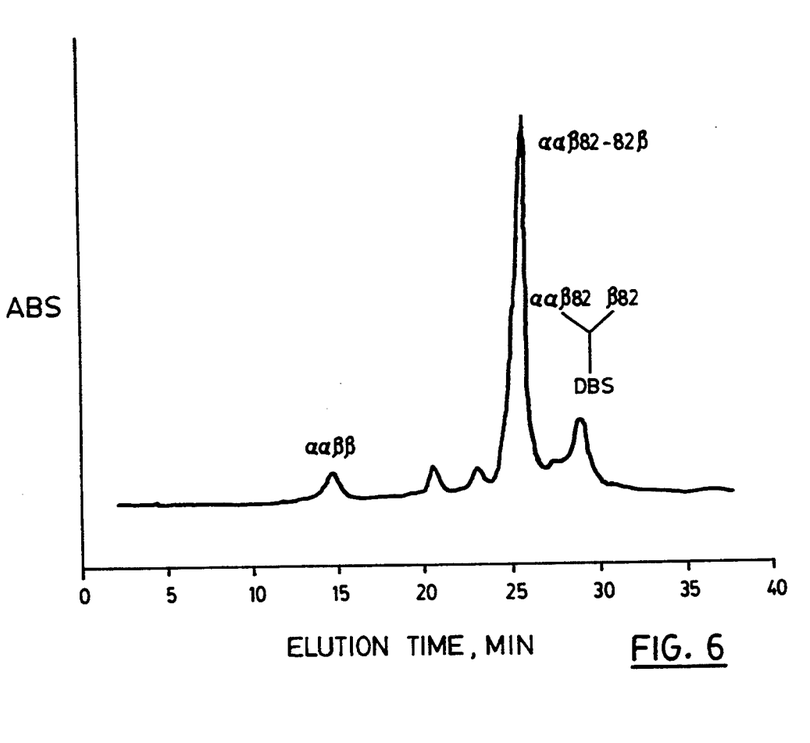
FIG. 6 is an AX-300 profile for reaction of TTDS with carbonmonoxyhemoglobin COHb at 60° C. for 2 hours, Example 3 below.

The reagent TTDS can be prepared in one of two ways. In its direct synthesis, illustrated in FIG. 1 of the accompanying drawings, triethylamine is reacted with 3,5-dibromosalicylic acid, followed by reaction with trimesoyl trichloride. This produces TTDS in relatively low yield. An improved synthesis, illustrated in FIG. 2 of the accompanying drawings, follows the general procedures of Delaney et al., Arch. Biochem. Biophys., 1984, 228, 627, to prepare trimesoyl-tris-(1-t-butoxycarbonyl-3,5-dibromosalicylate) by reaction of potassium t-butoxide with t-butyl-3,5-dibromosalicylate, followed by addition of tremesoyl chloride. TTDS is then formed by deprotecting the carboxyl groups, e.g. with trifluoroacetic acid. Much improved yields of TTDS are obtained by this procedure.

The invention is further described for illustrative purposes in the following specific examples.

SPECIFIC DESCRIPTION OF THE MOST PREFERRED EMBODIMENTS

Materials and Methods

Commercial reagents were utilized without further purification. Solvents were dried prior to use. Deuterated solvents were from MSD Isotopes Ltd. and the Aldrich Chemical Company. Organic reagents and solvents were purchased from Fisher Scientific. The purity of samples of newly synthesized materials was assessed by a combination of NMR spectroscopy, mass spectrometry, analytical thin layer chromatography, and elemental analysis. The latter was done by Galbraith Laboratories, Knoxville, Tenn.

Molecular Mechanics

HyperChem (version 1.9, from HyperCube division of Autodesk, Inc.), operating on a 486 computer (MS-DOS), was used to obtain energetic minima for iterative conformational perturbations based on several initially estimated structures of TTDS using mixed-gradient optimization. It was also used to visualize the structure of deoxyhemoglobin based on information from the Brookhaven Protein Data Bank.

Spectra and Kinetics

Proton and carbon NMR spectra were recorded on a Varian Gemini (200 MHx) spectrometer. Infrared spectra were recorded on a Nicolet 5DX FTIR spectrometer. UV spectra and kinetics were done on a Perkin-Elmer Lambda 2 spectrometer interfaced to a MS-DOS 386 computer. Spectra were collected with the Perkin-Elmer PECSS program and kinetics analyzed using GraFit (Erithacus Software, Ltd.).

Biochemical Materials

HPLC grade acetonitrile and water were obtained from Mallinckrodt and trifluoroacetic acid (TFA) was from Pierce Chemical Co. (Rockford, Ill.). Trypsin from Worthington Biochemical Co. (Freehold, N.J.) and staphylococcus aurous V* endoproteinase Glu-C from Boehringer Mannheim Biochemical (Indianapolis, Ind.) were used for enzymic digestion of globin chains. Sephadex G-25, DEAE-Sephacel and CM-Sephadex were from Pharmacia Fine Chemicals AB (Uppsala, Sweden). Other reagents for preparation of buffers and developers for the modifications of hemoglobin and for chromatography were all of analytical grade or better.

Hemoglobin was prepared using procedures as described, for example, by Kavanaugh et al., "Biochemistry" 1988, 27, 1804. Solutions were contained in a 50 mL round-bottom flask which was immersed in a water bath and connected to a rotary evaporator with the condenser replaced by a septum through which pass outlet and inlet tubes (for gas flow). Stock solutions of carbonmonoxyhemoglobin wee converted to oxyhemoglobin by photoirradiation under a stream of humidified oxygen for sixty minutes at 0° C. in a rotating flask. Oxyhemoglobin was converted to deoxyhemoglobin by passing a stream of humidified nitrogen over the oxyhemoglobin solution in the rotating flask for two hours at 35° C.

EXAMPLE 1

Direct Synthesis of TTDS

Triethylamine (1.45 g, 15 mmol) was added to a solution of 3,5-dibromosalicylic acid (2.00 g, 6.76 mmol) in anhydrous THF (25 mL) at room temperature. After stirring 10 minutes, a solution of trimesoyl trichloride (0.6 g, 2.3 mmol) was added dropwise to the reaction mixture. The solution was stirred at room temperature for two hours. The ppt was filtered off and the solvent removed in vacuo. The residue was partitioned between ethyl acetate (60 mL) and 0.1N HCl (100 mL). After separation, the organic phase was washed with 0.1N HCl ($2 \times 100$ mL), dried over $Na_2SO_4$ and concentrated in vacuo to give a white solid (2.25 g) which was characterized by $^1$HNMR as a mixture containing TTDS. A portion of this product (28 mg) was purified by HPLC (C-18 reverse phase column, acetonitrile (0.1% acetic acid) solvent). A small amount of pure TTDS was isolated (7.0 mg, 25% recovery). IR (KBr) 3416 (br.,s), 2355 (s), 1743 (s), 1002 (s) cm$^{-1}$, $^1$HNMR (acetone-d$_6$) $\delta$ 9.25 (s, 3H, ArH), 8.25 (AB, 6H, ArH), 4.40 (br.s, 3H, $CO_2H$). $-$CNMR (acetone-d$^6$) $\delta$ 164.01 (s), 163.02 (s), 148.59 (s), 140.64 (s), 137.20 (s), 135.16 (s), 132.18 (s), 128.17 (s), 120.69 (s), 120.50 (s); MS (negative FAB) 1043 (M$-$1).

The direct reaction of trimesoyl chloride with three equivalents of 3,5-dibromosalicylic acid in the presence of six equivalents of base gives an incomplete reaction.

Purification of the mixture using reverse phase PHLC provides the product in low yield.

EXAMPLE 2

Improved Synthesis of TTDS

The carboxyl-protected salicylate, trimesoyl-tris (1-t-butoxycarbonyl-3,5-dibromosalicylate, was prepared according to the general procedure of Delaney, Klotz and co-workers, op. cit. Potassium t-butoxide (0.30 g, 2.69 mmol) was added to a solution of t-butyl 3,5-dibromosalicylate (0.95 g, 2.69 mmol) in anhydrous THF (30 mL). The mixture was stirred at room temperature for 15 minutes. A solution of trimesoyl trichloride (0.24 g, 0.90 mmol) in tetrahydrofuran (10 mL) was added dropwise over 15 min. The reaction mixture was stirred overnight at room temperature. Ether (60 mL) was added, and the mixture was washed with water (2×100 mL). The organic phase was dried over $Na_2SO_4$, and concentrated in vacuo to give the product as a white solid (0.98 g, yield: 90%). $^1H$ NMR ($CDCl_3$) δ 9.32 (s, 3H, ArH), δ 8.01 (AB, 6H, ArH), 1.42 (s, 27H, $C(CH_3)_3$). FAB-MS 1213 (M+1). IR (KBr) 2980 (m), 1771 (s), 1722 (s), 1185 (s).

Trimesoyl tris(t-butoxycarbonyl-3,5-dibromosalicylate) so prepared (0.88 g, 0.73 mmol) was dissolved in anhydrous trifluoroacetic acid (20 mL) and kept at room temperature for 1 hour. Diethyl ether (20 mL) was added to induce crystallization. The solution was kept at 5° C. overnight. Product was collected by filtration (white crystals, 0.62 g, yield: 82%). Properties of the product synthesized by this route are identical to those of the purified compound prepared by the direct route.

Anal. calcd for $C_{30}H_{12}O_{12}Br_6$: C34.52, H 1.16, Br 45.93; found C 34.26, H 1.43, Br 45.58.

This experimental procedure involves protection of the carboxyl group of 3,5-dibromosalicylic acid as the t-butyl ester, coupling, and deprotection. Reaction of trimesoyl trichloride with potassium t-butyl 3,5-dibromosalicylate provides the carboxyl-protected coupling product in high yield (90%). The t-butyl group was readily removed with anhydrous trifluoroacetic acid to give analytically pure TTDS in 82% yield.

EXAMPLE 3

Reaction of TTDS with Hemoglobin

A solution of TTDS in buffer was added to the 1 mM hemoglobin solution described above so that the final concentrations of TTDS and hemoglobin were 1.0 mM and 0.5 mM, respectively, in 0.1M pH 7.2 MOPS buffer. The reactions were run at 35° C. or 60° C. for 2-3 hours in the rotating flask with hemoglobin in either the deoxy or carbonmonoxy form. For reactions with deoxyhemoglobin, TTDS was introduced into the reaction vessel under nitrogen. Nitrogen flowed continuously during the reaction over the hemoglobin solutions in the rotating flask to maintain the hemoglobin in the deoxy state. For reactions of carbonmonoxyhemoglobin, the hemoglobin solution was saturated with carbon monoxide and the reaction run without adding more gas. The reaction continued for 2 more hours after the completion of the addition of the reagents.

After reaction, the hemoglobin in each sample was separated from unreacted reagent by passing through a Pharmacia PD-10 Sephadex G-25 M column at 4° C. and then converted to carbonmonoxyhemoglobin by addition of carbon monoxide. Products were analyzed by a combination of polyacrylamide gel electrophoresis and ion exchange HPLC of intact tetramers, reverse phase HPLC of separated globin chains, and tryptic/-Glu-C digest of globin chains with peptide mapping.

Figure 7:
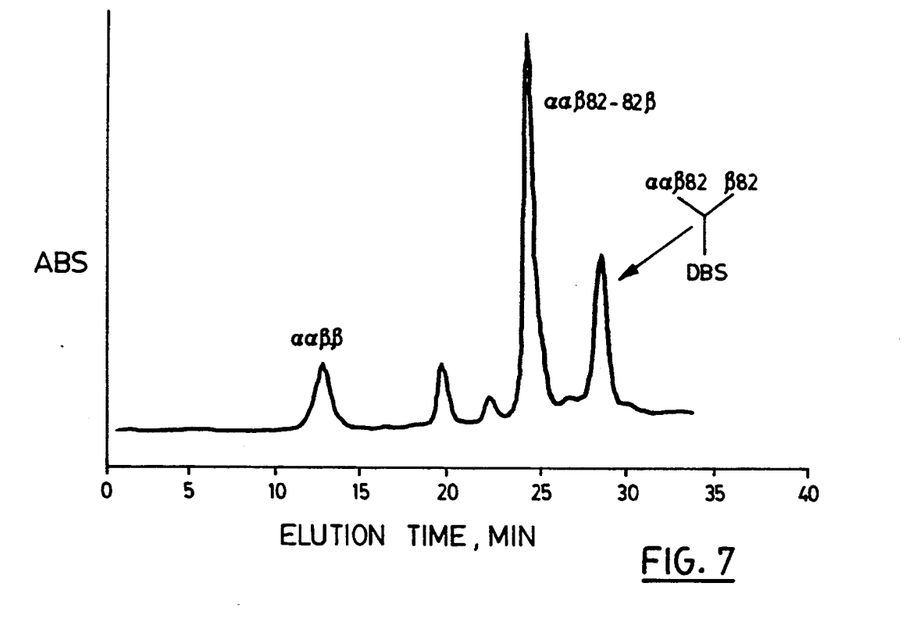
FIG. 7 is an AX-300 profile for reaction of TTDS with deoxyhemoglobin at 35° C. for two hours then analyzed after 15 days at 0° C., Example 3 below.
Figure 8:
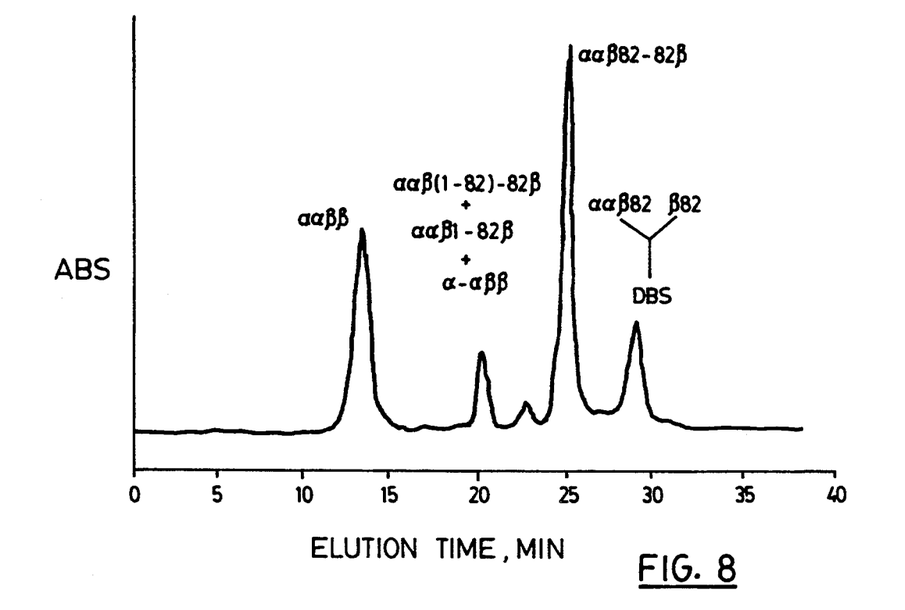
FIG. 8 is an AX-300 profile for reaction of TTDs with carbonmonoxyhemoglobin at 35° C. for two hours then analyzed after 15 days at 0° C., Example 3 below.

Deoxyhemoglobin and carbonmonoxyhemoglobin were treated with TTDS at 35° C. and at 60° C. The AX-300 ion exchange HPLC chromatograms of the reaction products (showing intact hemoglobin tetramers and modified tetramers) after two hours reaction (with reagents removed) are shown in FIGS. 3-6. In addition, the deoxyhemoglobin and carbonmonoxyhemoglobin reaction mixtures which had been run at 35° C. were stored on ice for 15 days and analyzed chromatographically after one week and after 15 days using the AX-300 column (FIGS. 7 and 8 are the chromatograms of the products after 15 days). The peaks were identified by globin chain separations on a C-4 reverse phase column and peptide pattern analysis. In all cases, products were identified by comparison with those obtained from the reaction of hemoglobin with trimesoyl tris(methyl phosphate) which had included amino acid analysis.

Analysis of the product distribution from the deoxyhemoglobin with TTDS shows that the primary cross-linked product has a trimesoyl group bridging Lysβ82 to the corresponding residue in the other β chain with the third group unreacted.

TTDS reacts more readily with deoxyhemoglobin than with carbonmonoxyhemoglobin at 35° C. but both form the same modified hemoglobins as products. The main difference is that deoxyhemoglobin produces much more of the β82-82-crosslinked hemoglobin with the third dibromosalicylate group still present. After 15 days at 0° C., however, the product from deoxyhemoglobin also has the third dimesoyl acyl group as the free acid. Complete hydrolysis occurs during this time rather than reaction with other amino groups of the protein. The reaction of TTDS with carbonmonoxyhemoglobin and with deoxyhemoglobin at 60° C. is complete after the initial two hour reaction period.

EXAMPLE 4

The rate of hydrolysis of TTDS was measured under the conditions in which the material is used to crosslink hemoglobin (0.1M MOPS, pH 7.2). The first ester hydrolysis follows first order kinetics with a half-life of 7.1 h ($k_{obs}=3.2\times10^{-5}s^{-1}$). The hydrolysis of the second and third ester groups is much slower. To estimate the reactivity of TTDS towards amino groups of hemoglobin, the reaction with n-hexylamine was measured (in 0.1M pH 7.2 buffer, $k_2=32M^{-1}sec^{-1}$). If, for example, hemoglobin is present at a concentration of 1 mM and TTDS is 2 mM, then the apparent initial first order rate constant for acylation of an amino group will be $3.2\times10^{-2} s^{-1}$, corresponding to a half life of about 20 s. The further reaction with other amino groups to form the crosslink should be rapid due to the reduced translational entropy of the bound reagent. The reaction of the reagent with accessible amino groups in hemoglobin should therefore be complete within a few minutes of mixing and hydrolysis is not a significant competing process.

EXAMPLE 5

Bioconjugation Procedure

One to two equivalents of a nucleophilic species, namely lysine, was added to a buffered solution of the modified hemoglobin and the solution stirred for two hours at 35° C. The product was isolated by gel filtration and analyzed by chromatography and ion-spray mass spectrometry. Chemical bonding of the lysine to the free carboxyl group on the residual TTDS was clearly evidenced.

EXAMPLE 6

Bioconjugation

Other compounds can be bound to the crosslinked Hb using the following general experimental conditions:

Immediately after the crosslinking reaction, a solution of the crosslinked Hb (in CO form, 0.3~1.4 mM, 2.0~20 mL, in 0.10M MOPS buffer, pH 7.2) and the compound to be introduced (30~500 mM) were incubated at 0°~25° C. for 2~72 h. The pH of incubation solution was adjusted, according to needs, within a range of 5.5~9.5. The progress of the reaction can be followed by HPLC chromatography (Vydac C4 column). After the reaction was finished, the reaction solution was passed through a sephadex column to remove unreacted small molecules. A pure sample of the desired Hb conjugate was obtained.

The following classes of molecules have been successfully conjugated to the crosslinked Hb by this procedure:

1) Polyhydroxylamines such as

Bis-Tris

2) Amino acids such as

Glycine

Lysine

3) Peptides such as

Gly-gly-gly

4) Enzyme cofactor analogs such as

Pyridinium nucleotide analog

Biotinyl hydrazide

FMN analog

5) Hormones such as

Norepinephrine

Epinephrine

We claim:

1. A process for preparing specifically crosslinked tetrameric hemoglobin by reacting hemoglobin with a chemical crosslinking agent, said crosslinked hemoglobin having crosslinks between the primary amino groups Lys-82 on the respective β sub-units and a free, chemically reactive group derived from the chemical crosslinking reagent, which comprises reacting hemoglobin with a crosslinking reagent corresponding to the general formula wherein R represents an aromatic hydrocarbon radical, and X, Y and Z are the same or different and each represents a bulky, aromatic, group with at least two electron withdrawing groups as substituents.

2. The process of claim 1 wherein the electron-withdrawing groups are selected from the group consisting of halogen and carboxylate and combinations thereof.

3. The process of claim 2 wherein the crosslinking reagent is trimesoyl tris(3,5-dibromosalicylate) so that the free, chemically reactive group is a carboxyl group.

4. The process of claim 3 wherein the hemoglobin is selected from the group consisting of human deoxyhemoglobin and human carbonmonoxylated hemoglobin.

5. The process of claim 3 including the further, subsequent step of reacting the free carboxyl group with an exogenous nucleophile.

6. The process of claim 5 wherein the exogenous nucleophile is an amine.

7. The process of claim 3 wherein the hemoglobin is selected from the group consisting of animal deoxyhemoglobin and animal carbonmonoxylated hemoglobin.

8. Specifically crosslinked tetrameric hemoglobin having crosslinking groups extending between and covalently bonded to primary amine groups Lys-82 on the respective $\beta$ sub-units, said crosslinking groups further including a carboxyl group available for reaction with an exogenous nucleophile.

9. Specifically crosslinked tetrameric hemoglobin according to claim 8 wherein the crosslinking group is the residue of reaction of trimesoyl tris(3,5-dibromosalicylate) with said primary amine groups.

* * * * *